(12) United States Patent
Brown et al.

(10) Patent No.: US 10,535,441 B1
(45) Date of Patent: Jan. 14, 2020

(54) METHOD OF IRRADIATING A TARGET

(71) Applicant: Mevex Corporation, Stittsville (CA)

(72) Inventors: David A. Brown, Dunrobin (CA);
David J. Hepworth, Ottawa (CA);
Simon J. Forknall, Ottawa (CA); Peter W. A. Brown, Almonte (CA); David M. Macrillo, Ottawa (CA); Kevin Murray Austin, Ottawa (CA)

(73) Assignee: MEVEX CORPORATION, Stittsville (CA)

( * ) Notice: Subject to any disclaimer, the term of this patent is extended or adjusted under 35 U.S.C. 154(b) by 0 days.

(21) Appl. No.: 16/039,976

(22) Filed: Jul. 19, 2018

Related U.S. Application Data (63) Continuation-in-part of application No. 13/192,061, filed on Jul. 27, 2011, now abandoned.
(Continued)

(30) Foreign Application Priority Data

Aug. 31, 2010 (CA) ..................... 2713972

(51) Int. Cl.
*G21G 1/12* (2006.01)
*G21K 1/093* (2006.01)
(Continued)

(52) U.S. Cl.
CPC ............... *G21G 1/12* (2013.01); *G21K 1/093* (2013.01); *A61N 5/1037* (2013.01);
(Continued)

(58) Field of Classification Search
CPC .......... H01J 2237/30472; H01J 37/304; H05H 15/00; G21K 1/00; G21K 5/10;
(Continued)

(56) References Cited

U.S. PATENT DOCUMENTS 2,815,450 A * 12/1957 Dickinson ................ H05G 1/62
315/500
2,959,700 A   11/1960 Campanile
(Continued)

FOREIGN PATENT DOCUMENTS

WO        9952587 A2   10/1999

OTHER PUBLICATIONS

U.S. Appl. No. 13/192,061, Final Office Action dated Feb. 1, 2017.
(Continued)

*Primary Examiner* — Lily C Garner
(74) *Attorney, Agent, or Firm* — Borden Ladner Gervais LLP; Louis B. Allard (57) ABSTRACT

A method of irradiating a target with a high power density irradiation beam is described. The method can use an irradiation system configured to output an irradiation beam through a vacuum window. The irradiation beam is scanned repetitively back and forth between two angular orientations of the irradiation beam as the irradiation beam strikes and traverses the vacuum window. The target is moved as the irradiation beam is scanned. The irradiation beam and the target are aligned. The scanning of the irradiations beam and the moving of the target are synchronized to each other. The scanning of the irradiation beam prevents localized overheating of the vacuum window and allows the irradiation beam to have a power density that would damage the vacuum window if the irradiation beam were not scanned.

19 Claims, 6 Drawing Sheets

Related U.S. Application Data (60) Provisional application No. 61/368,115, filed on Jul. 27, 2010.

(51) Int. Cl.

| | |
|---|---|
| *H05H 15/00* | (2006.01) |
| *G01N 29/275* | (2006.01) |
| *A61N 5/10* | (2006.01) |
| *G01N 21/89* | (2006.01) |
| *G01N 23/16* | (2018.01) |

(52) U.S. Cl.
CPC ........ *A61N 5/1042* (2013.01); *G01N 21/8901* (2013.01); *G01N 23/16* (2013.01); *G01N 29/275* (2013.01); *G01N 2201/104* (2013.01); *H05H 15/00* (2013.01)

(58) Field of Classification Search
CPC ...... G21G 1/12; A61N 5/1042; A61N 5/1037; A61N 5/1044; G01N 21/8901; G01N 23/16; G01N 29/275; G01N 2201/104; G02B 7/1827
See application file for complete search history.

(56) References Cited

U.S. PATENT DOCUMENTS

| | | | |
|---|---|---|---|
| 4,980,901 A | 12/1990 | Miller | |
| 5,449,916 A | 9/1995 | Smyth et al. | |
| 5,714,875 A | 2/1998 | Lawrence et al. | |
| 5,847,401 A | 12/1998 | McKeown et al. | |
| 5,849,252 A | 12/1998 | Wakamoto et al. | |
| 6,333,966 B1 | 12/2001 | Schoen | |
| 6,429,426 B1 | 8/2002 | Doering | |
| 6,472,677 B1 | 10/2002 | Rodriguez et al. | |
| 6,628,750 B1 | 9/2003 | Korenev | |
| 6,992,310 B1* | 1/2006 | Ferrara | H01J 37/3171 250/442.11 |
| 7,274,026 B2 | 9/2007 | Bol et al. | |
| 7,884,936 B2 | 2/2011 | Manassen | |
| 8,791,435 B2 | 7/2014 | Balakin | |
| 2008/0037609 A1* | 2/2008 | Nagai | H01S 3/2308 372/57 |
| 2009/0041198 A1* | 2/2009 | Price | G21K 1/02 378/147 |
| 2009/0065693 A1 | 3/2009 | Safa | |
| 2009/0213977 A1* | 8/2009 | Russell, II | G21G 1/02 376/170 |

OTHER PUBLICATIONS

U.S. Appl. No. 13/192,061, Final Office Action dated Feb. 1, 2018.
U.S. Appl. No. 13/192,061, Non-Final Office Action dated Aug. 18, 2016.
U.S. Appl. No. 13/192,061, Non-Final Office Action dated Sep. 29, 2017.

* cited by examiner

METHOD OF IRRADIATING A TARGET

FIELD

The present disclosure relates generally to particle accelerators. More particularly, the present disclosure relates to a method of irradiating a target.

BACKGROUND

In many applications there is a need to focus or concentrate all of a particle beam's energy on target volumes. In other cases only a portion of the total beam energy is useful for effecting the change desired and the remainder is waste. The waste is heat, which can be difficult and expensive to deal with. Disposing of the waste heat can be so difficult or expensive that a particular application may be impractical or impossible.

For example, $^{99}$Mo, which is the parent of $^{99m}$Tc, an isotope widely used for medical diagnostic purposes, can be produced by the photonuclear transmutation of $^{100}$Mo. The process requires bremsstrahlung to interact with $^{100}$Mo. "bremsstrahlung" (meaning braking radiation) is the radiation which is emitted when electrons are decelerated or braked when they are fired at a target. Accelerated charges give off electromagnetic radiation, and when the energy of the bombarding electrons is high enough, that radiation is in the x-ray region of the electromagnetic spectrum. Bremsstrahlung is characterized by a continuous distribution of radiation which becomes more intense and shifts toward higher frequencies when the energy of the bombarding electrons is increased. The more intense the bremsstrahlung, the higher the specific activity of the $^{99}$Mo (in Curies/gram). To produce bremsstrahlung of sufficient intensity to create photonuclear transmutation of $^{100}$Mo requires very high electron beam intensity at very high kinetic energy. Providing such a high electron beam intensity at high kinetic energy is readily achievable.

However, while producing a beam of sufficient intensity and energy is readily achievable, the means to deliver the necessary intensity of bremsstrahlung to a material intended for photonuclear transmutation has not heretofore been practicable. To extract a high energy, high power, and high areal power density electron beam from its acceleration environment (which is high vacuum), through a vacuum barrier, and through atmosphere to a bremsstrahlung converter suffers several impediments. First, in high power operation, only about half the beam power is converted to useable bremsstrahlung; the remainder is waste heat. Due to the rate of power absorption in the vacuum barrier and the converter, this waste heat will destroy most practical materials of which the vacuum barrier and the converter can be made.

It is, therefore, desirable to provide an improved means to extract a high power density particle beam from a particle accelerator for application to a material.

SUMMARY OF THE DISCLOSURE

In a first aspect, there is provided a method of irradiating a target. The method comprises: scanning an irradiation beam repetitively back and forth between two angular orientations of the irradiation beam as the irradiation beam strikes a vacuum window and traverses the vacuum window; moving the target repetitively back and forth between two target positions; aligning the target and the irradiation beam to each other; synchronizing, to each other, the scanning of the irradiation beam and the moving of the target to maintain alignment between the irradiation beam and the target during the scanning of the irradiation beam and the moving of the target; and shutting down the irradiation beam when a stop criterion is met.

In a further aspect, there is provided another method of irradiating a target. This method comprises: providing a particle accelerator, the particle accelerator having a vacuum window; controlling the particle accelerator to generate an irradiation beam and to scan the irradiation beam repetitively back and forth between two angular orientations of the irradiation beam as the irradiation beam strikes the vacuum window and traverses the vacuum window; mounting the target to a translation stage and controlling the translation stage to move the target repetitively back and forth between two target positions; aligning the target and the irradiation beam to each other; synchronizing, to each other, the scanning of the irradiation beam and the moving of the target to maintain alignment between the irradiation beam and the target during the scanning of the irradiation beam and the moving of the target; and shutting down the irradiation beam when a stop criterion is met.

BRIEF DESCRIPTION OF THE DRAWINGS

Embodiments of the present disclosure will now be described, by way of example only, with reference to the attached Figures, wherein.

DETAILED DESCRIPTION

The present disclosure describes methods and apparatuses which allow concentrated radiation power from a particle accelerator to be spread out over places where it would otherwise cause undesirable effects and to concentrate it where it is intended to cause desirable effects.

The present disclosure generally describes a method of effecting a chemical, physical or transmutational change in a target material using a high power particle beam concentrated on the target material. The particle beam is scanned repetitively back and forth between two angular orientations of the particle beam as the particle beam strikes a vacuum window and traverses the vacuum window. This scanning prevents overheating and damaging the vacuum window, which would occur if the particle beam were not scanned but instead struck (impinged on) the vacuum window in the same fixed location. Movement between the target and the scanned beam is then synchronized to cause the scanned beam to persistently or continuously strike the target to effect the chemical, physical or transmutational change, thereby concentrating the beam on the target.

According to an embodiment, the present disclosure is directed to an apparatus to move a target material in synchronization with the impingement of an electron beam on a bremsstrahlung converter, so that the material is always exposed to the full intensity of the bremsstrahlung produced in the converter. The particle beam is a high power, highly concentrated electron beam generated in a vacuum system by, for example, a linear accelerator. The electron beam is scanned across the vacuum barrier (e.g. a titanium window) of a scan horn and then extracted from vacuum system. The scanned beam can then be converted to bremsstrahlung, such as by striking a tungsten or tungsten carbide plate. The useful portion of the beam (bremsstrahlung) can then be applied to the final target material by causing the target material to move in synchronization with the electron beam movement on the converter so that the full intensity of the bremsstrahlung is always concentrated on the intended target material. The target can be controlled to follow the scanned beam, or the scanned beam can be controlled to follow the target.

The present technique can be used to provide a highly concentrated electron or x-ray beam for use in, for example, nuclear transmutation for isotope production, such as medical isotope production; radiochemistry experiments; and materials studies.

Embodiments of the present system will now be described with reference to the figures. The system is generally designed to synchronize the movement of the target, such as an isotope target, and the electron beam to maximize the exposure of the target to the x-rays produced in the converter. While the embodiments discussed below use a linear particle accelerator, any suitable particle accelerator in which the beam can be steered or scanned can be used, as will be clear to those of skill in the art.

Figure 1:
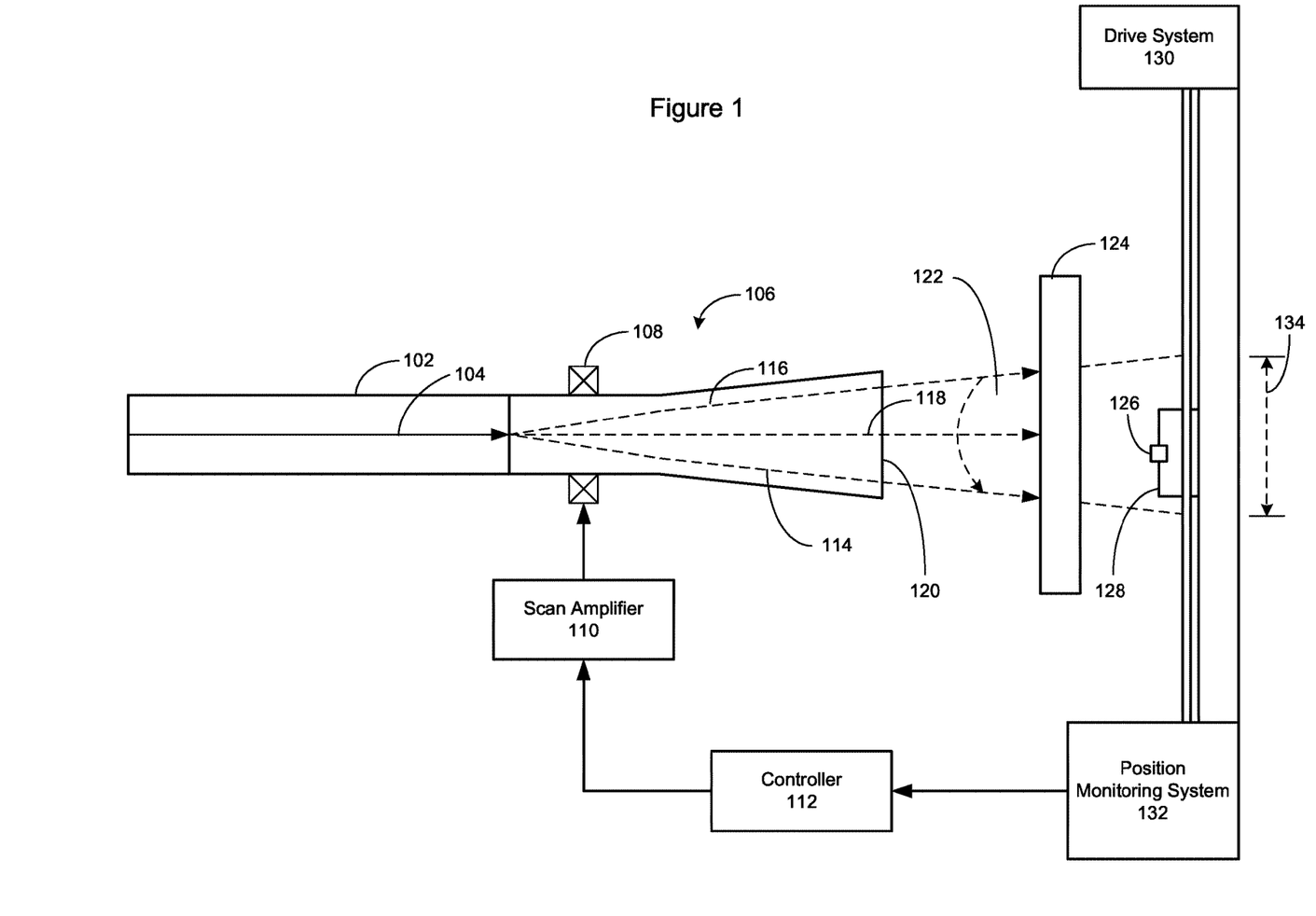
FIG. 1 shows a side view in cross-section of an embodiment of a system according to the present disclosure.

FIG. 1 shows a side view in cross-section of an embodiment of the system where the position of the target controls the scanning of the beam. A conventional particle accelerator 102, such as a linear particle accelerator or linac, which provides, for example, a 20 MeV 20 kW electron beam of less than 10 mm diameter at the electron window, can be used.

The beam of accelerated electrons 104 is received from the accelerator 102 and enters scan horn 106, both of which are under high vacuum. A scanning magnet assembly, comprising electromagnets 108 and a scan amplifier 110 deflects electron beam 104 in an amount proportional to a current through the electromagnets 108. The current is provided by scan amplifier 110, under the control of controller 112, as will be described further below. Path 114 represents a maximum deflection in the lower direction, path 116 represents a maximum deflection in the upper path, and path 118 represents the direction of beam 104 with essentially no current passing through scanning magnet assembly.

The beam is scanned to ensure the integrity of the titanium window 120, or other vacuum window (barrier), on the scan horn 106. As will be understood by those of skill in the art, the particular geometry and control of the scanning magnet assembly will determine the scan pattern of the electron beam 102 across the window 120. For the purposes of the present description, the pattern is assumed to be a vertical scanning pattern having an arc of travel from the maximum deflection in the lower direction (path 114) to the maximum deflection in the upper direction (path 116), but any appropriate orientation of scan can be used, as appropriate to a particular application or configuration.

In an embodiment, the electrons of the scanned beam 122 exit the scan horn 106 into the atmosphere and strike a converter plate 124, such as a bremsstrahlung converter, where they are converted to x-ray energy. The typical materials for this conversion plate 124 are dense metals such as tungsten or tantalum, since the conversion efficiency is directly proportional to the atomic number of the conversion material, and the x-ray intensity is a function of the thickness of material that the electrons must pass through.

The x-rays exit the converter plate 124 with essentially the same scan pattern as the scanned beam, and then strike a target assembly comprising a target 126 that is mounted on a target mount 128. The target assembly is mounted on a translation device 127 that, in the illustrated embodiment, is comprised of a driveshaft 129 and a drive system 130 that translates the target mount 128 along a path 134 substantially identical to the arc of travel of the scanned beam 122. In an embodiment, the translation device 127 uses a servo motor to drive the target through a cam system. A position monitoring system 132 is provided to monitor the position of the target assembly. The position monitoring system 132 can include any suitable transducing device(s), such as optical transducers, a driveshaft resolver or other suitable optical, rotary, or linear position transducers or encoders as are well known in the art.

The translation device 127 is configured to move the target mount 128 (and the target mounted thereon) along a straight line. However, translation devices configured to move a target along curved lines (e.g., an arc of a circle or a contour of an ellipse), are also considered to be within the scope of the present disclosure.

Generally, the magnetic scanning system, including scan magnets 108 and scan amplifier 110, can be driven by the position monitoring system 132 monitoring the position of the target mounted on the translation device.

The position monitoring system 132 senses the position of the target assembly. The sensed position is provided to the controller 112, which, in turn, controls the scan amplifier 110 of the scanning magnet assembly to ensure that the position of the beam and the position of the target 126 coincide. The controller 112 can be a general purpose computer or a digital signal processor, or other suitable controller depending on the particular choice and configuration of the position monitoring system 132, the scan amplifier 110, and optionally the drive system 130. For example, according to an embodiment, a shaft resolver/encoder can be shaft-mounted behind the servo motor which drives the target assembly. The target assembly position can be determined accurately by reading position data from the shaft resolver and driving the scan amplifier 110 accordingly, such as through a variable analog voltage, provided by a digital/analog converter, which drives the electron beam in synchronization with the movement of the target.

Figure 2:
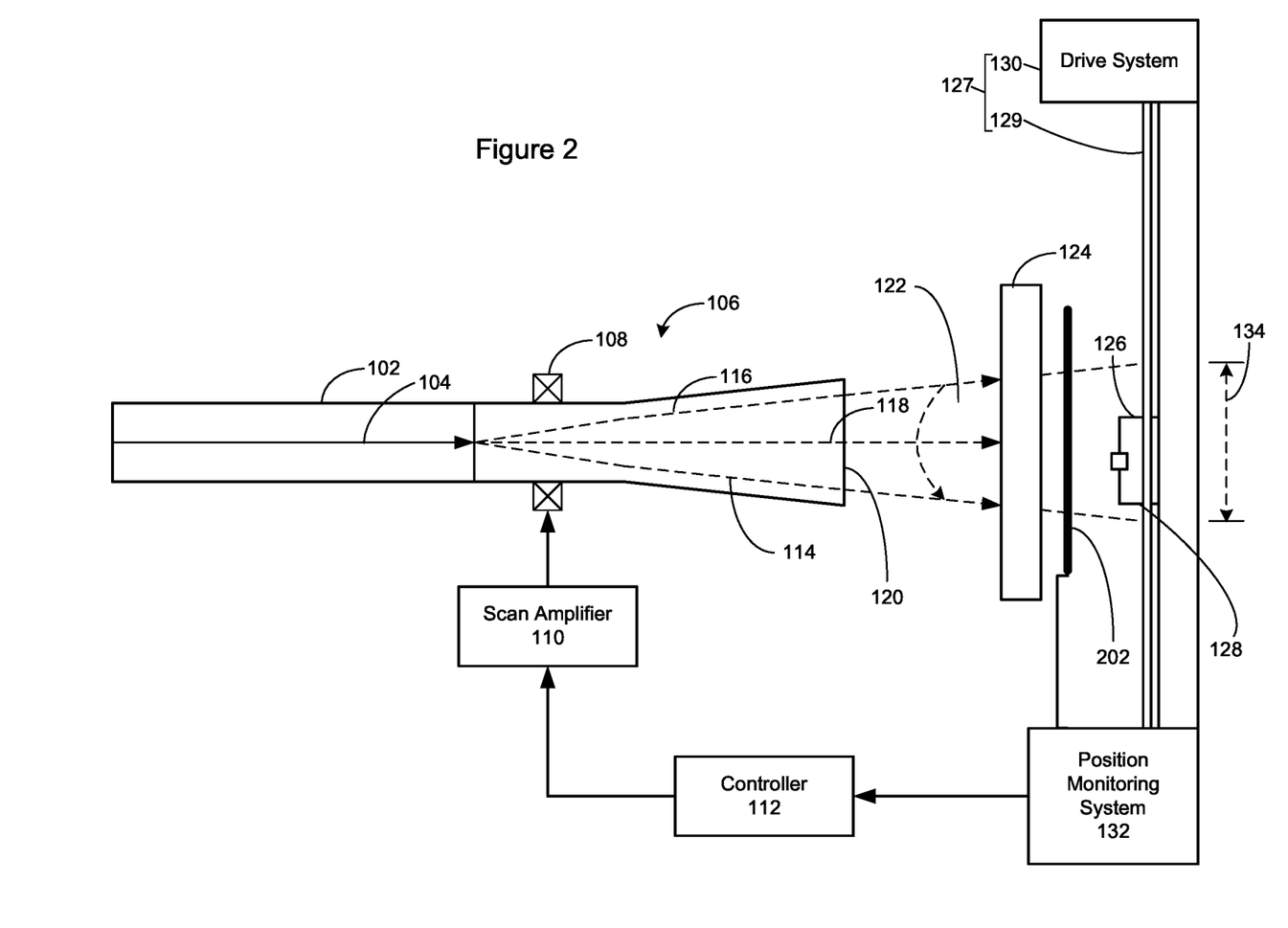
FIG. 2 shows a side view in cross-section of a further embodiment of a system according to the present disclosure.

FIG. 2 shows a side view in cross-section of an embodiment of a system according to the present disclosure where the scanning of the beam controls the position of the target. The details of the components, which are substantially identical to those of FIG. 1 will not be repeated. The difference in the system of FIG. 2 is that the translation device (through the drive system 130) is driven synchronously with the scanning of the beam, as opposed to driving the beam in synchronization with the target assembly position. In this embodiment, the position of the beam is monitored by a beam position monitor 202. The controller 112 then uses the beam position to control the speed of the drive system 130, such as by changing the drive frequency setpoint for the servo motor described above.

Figure 3:
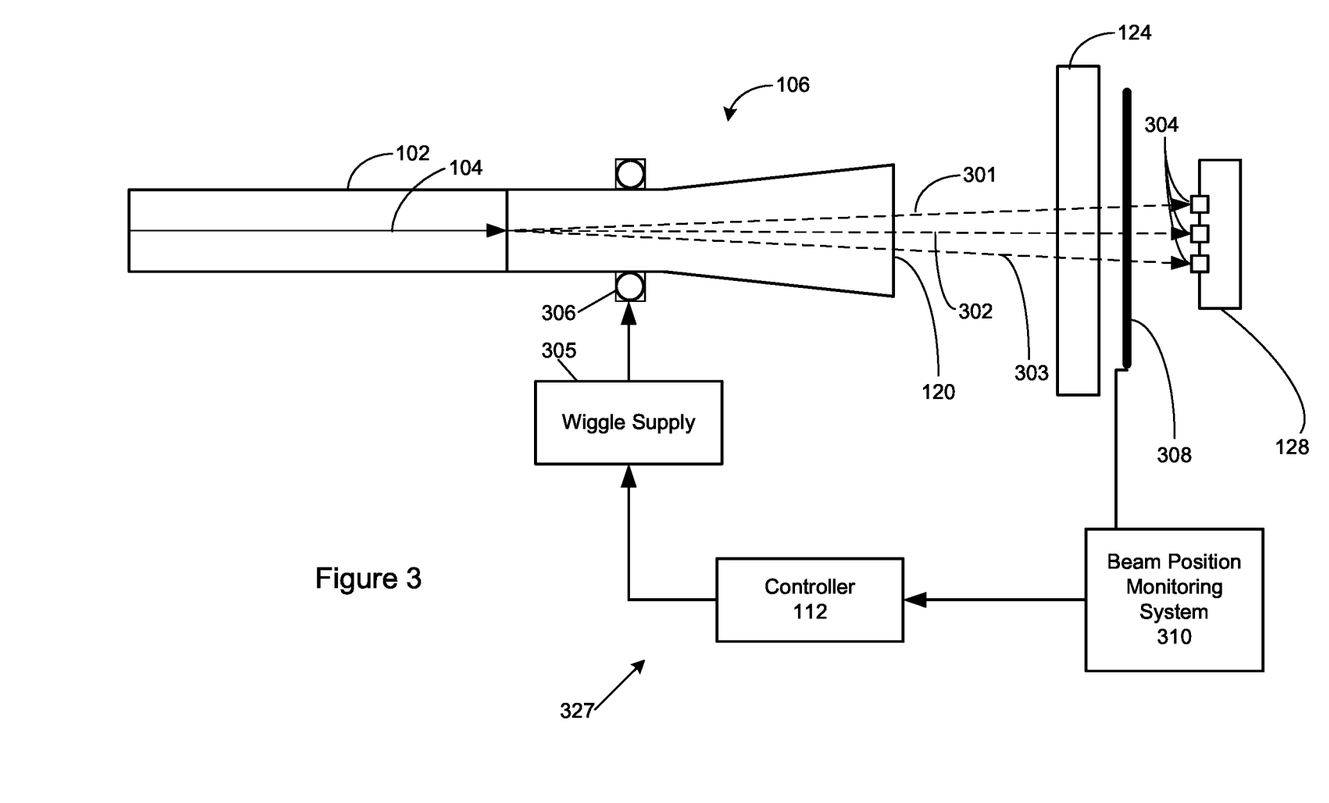
FIG. 3 as a top view in cross-section of another embodiment of a system according to the present disclosure.

FIG. 3 shows a top view in cross-section of a system according to a further embodiment, where, in addition to scanning the beam vertically using the scanning magnet assembly, the beam is also "wiggled" or translated laterally in a stepwise manner (as shown by the paths 301, 302 and 303, thereby permitting multiple targets 304 to be irradiated. This lateral translation can be achieved using "wiggle" magnets 306, acting perpendicular to the magnets 108 (not shown—see FIG. 2), a wiggle supply 305 to control current to the magnets 306 and a beam position monitor 308 and beam position monitoring system 310 to monitor the lateral position of the scanned beam. The magnets 306, the wiggle supply 305, the beam position monitor, and the beam position monitoring system form a beam shifting assembly.

Figure 4:
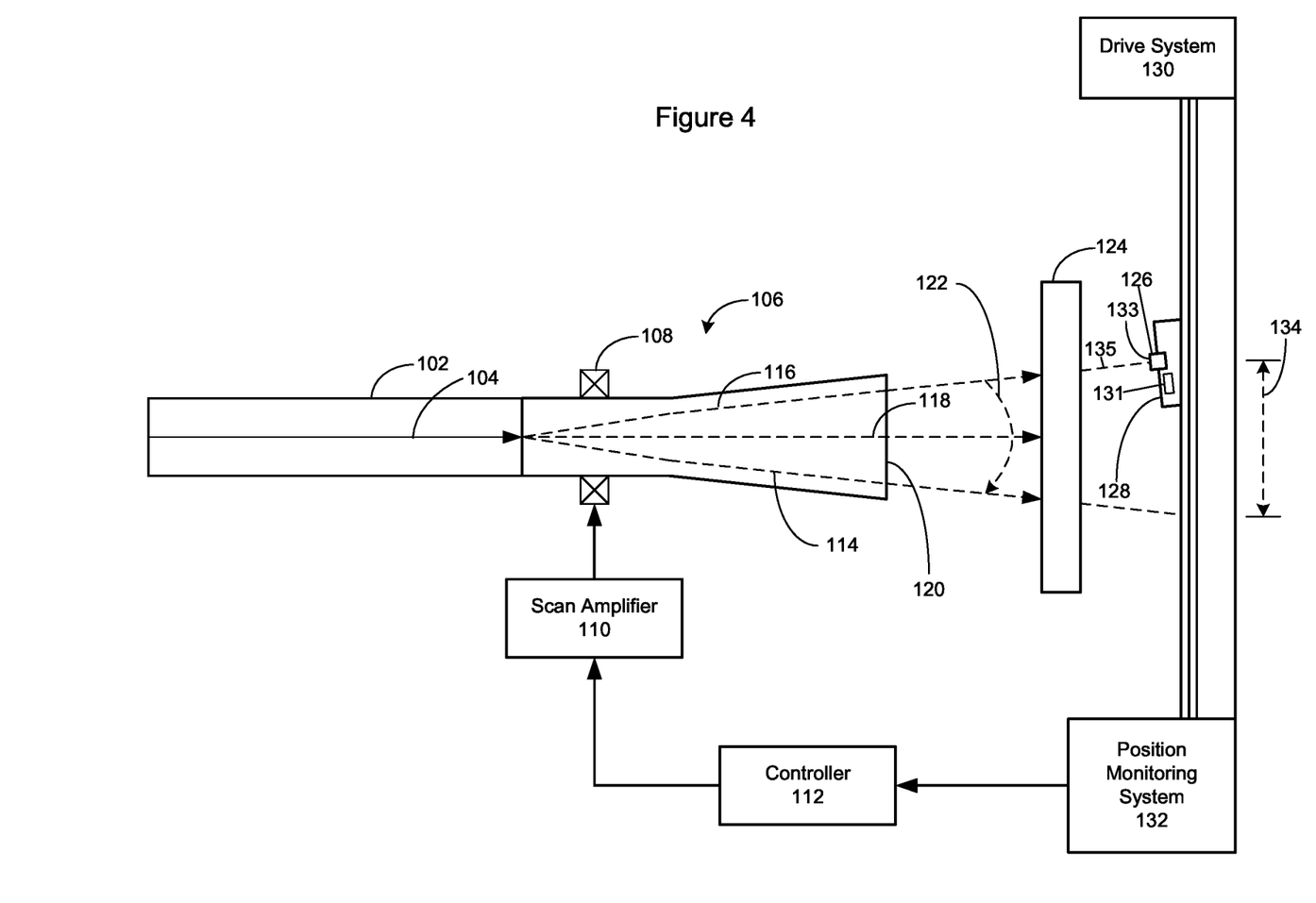
FIG. 4 shows a side view in cross-section of yet another embodiment of a system according to the present disclosure.

In a further embodiment shown at FIG. 4, the angle of the target mount 128 can be controlled by an attitude control assembly 132 that is configured to maintain a constant angle between a target face 133 of the target material (target 126) and a centerline 135 of the scanned concentrated beam. For example, the target mount 128 can be mounted on a mechanical control arm, under servo control, that can adjust the angle of the target mount 128 based on its position along the path 134.

It is known that high power density irradiation of a target can be carried out by opening an accelerator system and placing the target in the accelerator system, in alignment with the irradiation beam. The accelerator system is then closed and pumped out to a desired vacuum level. After irradiation of the target, the vacuum is broken and the accelerator system opened to retrieve the irradiated target. This is a time consuming process that leaves the accelerator system prone to contamination. The following provides an alternative.

Figure 5:
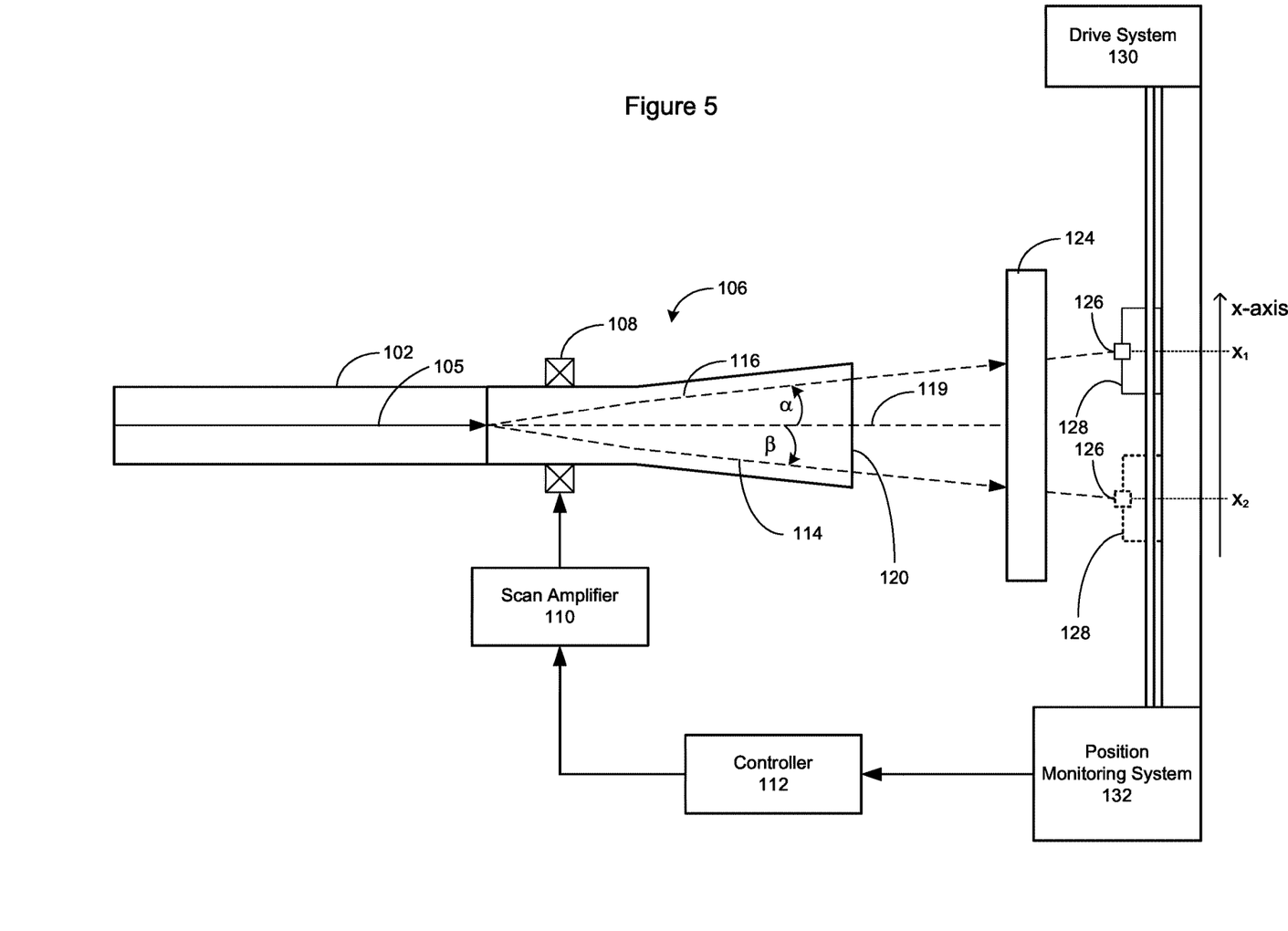
FIG. 5 shows is side view in cross-section of an additional embodiment of a system according to the present disclosure.

FIG. 5 shows a side view in cross-section of an embodiment of a system according to the present disclosure. The accelerator 102 accelerates particles (for example, electrons, hydrogen ions, etc.) to obtain an irradiation beam 105, which is directed towards the vacuum window 120. The irradiation beam 105 is scanned repetitively back and forth between two angular orientations $\alpha$ and $\beta$, which, in this example, are measured with respect to a centerline 119. The centerline 119 in this example is collinear with the irradiation beam 105 when the particle beam 105 is not subjected to any steering force. The angular orientations $\alpha$ and $\beta$ can have any suitable values, which, as will be understood by the skilled worker, are limited by the geometry of the scan horn 106. It is not required that the two angular orientations have the same absolute value (e.g., $\alpha$=+20° and $\alpha$ and $\beta$=−20°). The two angular orientations can be measured with respect to any suitable reference line and not necessarily with respect to the centerline 119.

The repetitive back and forth scanning of the irradiation beam 104 between the two angular orientations is carried out by a scanning magnet assembly (comprising the electromagnets 108 and the scan amplifier 110) that deflects irradiation beam 105 in an amount proportional to a current through the electromagnets 108. The current is provided by the scan amplifier 110, under the control of the controller 112.

As the irradiation beam is repetitively scanned back and forth between the two angular orientations, the target 126 is moved repetitively between two target positions shown as $x_1$ and $x_2$. The target 126 and the irradiation beam 105 can be aligned to each other and their movements synchronized to maintain alignment between the irradiation beam 105 and the target 126. In the present example, the alignment between the irradiation beam 105 and the target 126 is such that when the irradiation beam 105 is at the angular orientation $\alpha$, the target 126 is at the position $x_1$ and when the irradiation beam 105 is at the angular orientation $\beta$, the target 126 is at position $x_2$. The synchronization is such that the alignment between the irradiation beam 105 and the target 126 is maintained at $x_1$, $x_2$, and at all positions, between $x_1$ and $x_2$, as the positions become occupied by the target 126.

As described above in relation to other embodiments of the present disclosure, the movement (position) of the irradiation beam can be synchronized to the movement (position) of the target or vice versa.

In the example of FIG. 5, the irradiation beam 105 strikes the converter plate 124 rather than the target 126 as it would in absence of the converter plate 124. In this example, it is bremsstrahlung generated by the irradiation beam 105 striking the converter plate 105 that strikes the target 126.

Advantageously, because the irradiation beam 105 is scanned repetitively back and forth between the angular orientations $\alpha$ and $\beta$, the areal power density of the irradiation beam (e.g., watts per cm$^2$) can be adjusted to a value that would damage the vacuum window 120 and/or the converter plate 124 if the irradiation beam 105 were not scanned at all and irradiated the same area of the vacuum window 120 and/or the same area of the converter plated 124 for an extended time period (exceeding a damage threshold time period). As will be understood by the skilled worker, the damage threshold time period may be different for the vacuum window 120 and the converter plate 124. The damage threshold time period can depend on the type of particles that constitute the irradiation beam 105, on the material of which the vacuum window 120 and the converter plate 124 are made and on the thickness of the vacuum window 120 and the thickness of the converter plate 124. As will be understood by the skilled worker, the durability of the vacuum window 120 and/or the converter plate 124 can be expressed not only in units of areal power density: watts/cm$^2$, but also in units of areal energy density: joules/cm$^2$, units of areal current density: amperes/cm$^2$, or any other suitable units.

By scanning the irradiation beam 105 repetitively back and forth between the angular orientations $\alpha$ and $\beta$, the heat generated in the vacuum window 120 and/or the converter plate 124 as a result of the irradiation beam 105 interacting (striking and/or traversing) with the vacuum window 120 and/or the converter plate 124 is not confined to the same area on the vacuum window 120 and/or the converter plate 124 for a prolonged time period. Rather, the heat is spread along the path traced by the irradiation beam 105 on the vacuum window 120 and the converter plate 124.

The alignment of the irradiation beam with the target or with the same area of the target can be maintained to an acceptable level during the repetitive back and forth scanning of the irradiation beam and the movement of the target. In some transmutation applications, the irradiation beam misalignment with a target can be inferred by measuring the yield of the transmutated material and comparing the measured yield with an expected yield, calculated based on the experimental conditions. The alignment can subsequently be adjusted.

As mentioned elsewhere in this disclosure, certain applications require a high power density irradiation beam striking a target for a prolonged period of time. For example, in the field of nuclear medicine, radiation sources can be obtained through photonuclear transmutation of a target (comprising elements that can be transmutated) by irradiating the target with bremsstrahlung. The system of FIG. 5 can be used in this type of application. In this scenario, the generation of the required bremsstrahlung is achieved by producing a high power density irradiation beam 105 striking the converter plate 124, which in turn generates the required x-ray radiation. The required power density of the irradiation will in most cases be greater than the power density that can be sustained by the vacuum window 120 and/or the converter plate 124 for any period of time that would be required to effect transmutation of the target in a scenario where the irradiation beam is not scanned.

Because of the repetitive back and forth scanning of the irradiation beam, the alignment of the irradiation beam with the target, and the synchronization of scanning movement of the irradiation beam with the movement of the target, the transmutation of the target can be achieved without damaging the vacuum window 120 and/or the converter plate 124.

Examples of transmutation include the transmutation of molybdenum 100 to molybdenum 99 via the photonuclear reaction of bremsstrahlung ejecting a neutron from molybdenum 100. Another example is the transmutation of zinc 68 to copper 67. There are many others, some of them useful as diagnostic imaging radiopharmaceuticals and others for targeted radiotherapy. For example, Actinium 225 can be produced by photonuclear transmutation of Radium 226. Confirmation that a target has been transmutated can be obtained, after irradiation of the target, using conventional gamma spectroscopy methods. The yield of the desired material can be calculated accurately when the alignment tolerances of the irradiation beam with respect to target is controlled to known and acceptable amounts during irradiation.

Further, the present disclosure allows for the irradiation beam to be used to effect a physical transformation of the target by operating the system of FIG. 5 with or without the converter plate. Examples of a physical transformation include melting a portion of the target, vaporizing a portion of the target, increasing the density of a portion of the target, modifying the crystalline structure of a portion of the target, etc. Furthermore, the present disclosure allows for the irradiation beam to be used to effect a chemical transformation of the target.

Figure 6:
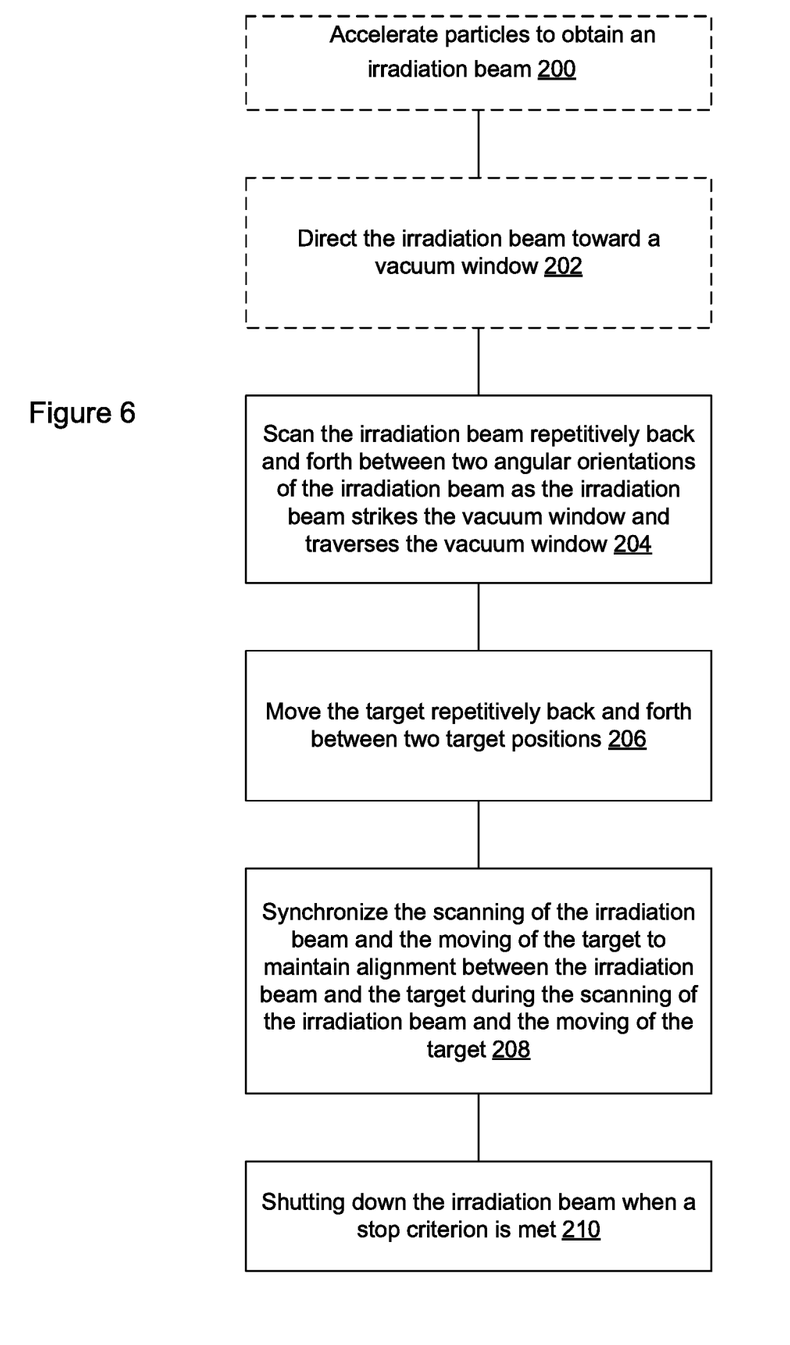
FIG. 6 shows a flow chart of a method of irradiating a target in accordance with an embodiment of the present disclosure.

FIG. 6 shows a flowchart of a method of irradiating a target in accordance with the present disclosure. At action 200, particles (for example electrons) are accelerated to obtain an irradiation beam. At action 202 the irradiation beam is directed toward a vacuum window. At action 204, the irradiation beam is scanned repetitively back and forth between two angular orientations as the irradiation beam strikes the vacuum window and traverses the vacuum window. At action 206, the target is moved repetitively back and forth between to target positions. At action 208, the target and the irradiation beam are aligned to each other. At action 210, synchronization of the scanning of the irradiation beam and the moving of the target is carried out in order to maintain alignment between the irradiation beam and the target during the scanning of the irradiation beam and the moving of the target. Finally, the irradiation of the target ends at action 210, when a stop criterion is met. That is, the irradiation beam is shutdown when the stop criterion is met. The stop criterion can include, for example, any of: an irradiation dose received at the target, a pre-determined irradiation duration; a desired amount (expressed as, for example, yield, volume, mass) of transmutated material; a desired amount (expressed as, for example, yield, volume, mass) of material obtained through a chemical reaction occurring during irradiation of a target; a desired amount (expressed as, for example, yield, volume, mass) of material obtained through a physical reaction occurring during irradiation of a target. The term "amount" can also be referred to as "extent" expression "desired amount" can also be referred to as "desired extent".

Advantageously, the present disclosure allows for the use of a conventional accelerator system in high power density applications without damaging the vacuum window and/or the converter plate. Additionally, as the present disclosure does not require the target to be placed in the same vacuum enclosure as the accelerator portion of the accelerator system, there is a substantial decrease in the time required to irradiate the target and a reduction in the risk of contamination of the accelerator system.

It is also contemplated that a single accelerator can be used to provide electron beam power to multiple target stations, in one or more rooms containing scanning equipment and a target translation device. Multiple target stations would allow continuous accelerator operation and finished target handling at stations other than the currently operating station. Suitable magnetic containment, redirection and kicker systems can be provided to guide the electron beam to appropriate stations or rooms.

The present disclosure allows for a very high average power electron beam to traverse the vacuum barrier and produce bremsstrahlung for beneficial purposes, such as chemical, physical or transmutational change, without compromising the integrity of the vacuum barrier or the converter. There are many possible uses for the apparatus and method described herein. For example, the method and system can be used to irradiate $^{100}$Mo by bremsstrahlung to transmutate it into $^{99}$Mo, which is the decay parent of $^{99m}$Tc, a useful and widely used medical diagnostic imaging isotope. The photonuclear transmutation of $^{134}$Xe into $^{131}$I by the same method is another example. Many other photonuclear transmutations are known, and the present disclosure can be extended to use in any of these applications with suitable modifications, as will be apparent to anyone of skill in the art. It may become possible to irradiate a specific material in order to produce neutrons during the irradiation and to use the generated neutrons in further nuclear applications.

As will be appreciated by those of skill in the art, the present disclosure has many advantages over the prior art. The method and apparatus provide a means to concentrate an electron beam directly on a target achieving very high power areal density without having the irradiation beam strike the vacuum window and/or the converter plate at the same spot for any prolonged period of time. This present disclosure provides a means to alleviate the limitations of the prior art by distributing the average electron beam power over a much larger area of the vacuum barrier and the converter thereby reducing the areal power density on both. Consequently the thermal stresses in both are reduced below the threshold of destruction.

In particular, the method and apparatus provide a means to concentrate high power, high intensity bremsstrahlung on at least one target material while diverting unwanted heat from the target material. The apparatus permits the use of conventional vacuum barriers, while protecting the barrier from thermal damage. Similarly, simply cooled bremsstrahlung converters can be used. The target material is also protected from damage due to unwanted impingement of high power, high intensity electron beams. By controlling the scanning of the beam and/or the movement of the target material, the target material can also be irradiated from a variety of directions.

The present disclosure permits more than one target to receive the desired bremsstrahlung. It also provides a means to avoid use of exotic bremsstrahlung converter materials and irradiation configurations. It also avoids location of a bremsstrahlung converter inside the acceleration vacuum envelope. It also avoids the use of a bremsstrahlung converter as the vacuum barrier.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of irradiating a target, the method comprising:
    scanning an irradiation beam repetitively back and forth between two angular orientations of the irradiation beam as the irradiation beam strikes a vacuum window and traverses the vacuum window;
    moving, along a straight line, the target repetitively back and forth between two target positions;
    aligning the target and the irradiation beam to each other;
    synchronizing, to each other, the scanning of the irradiation beam and the moving of the target along the straight line to maintain alignment between the irradiation beam and the target during the scanning of the irradiation beam and the moving of the target;
    shutting down the irradiation beam when a stop criterion is met.

2. The method of claim 1, wherein:
    the irradiation beam has an areal power density;
    the vacuum window has an areal power density threshold beyond which the vacuum window fails when subjected to, at a fixed position on the vacuum window, the power density beyond a pre-determined irradiation duration;
    the scanning of the irradiation beam between the two angular orientations of the irradiation beam results in a delivered power density lower than the power density threshold at all positions of the window subjected to the irradiation beam.

3. The method of claim 1, wherein:
    the irradiation beam has an areal energy density;
    the vacuum window has an areal energy density threshold beyond which the vacuum window fails when subjected to, at a fixed position on the vacuum window, the areal energy density beyond a pre-determined irradiation duration;
    the scanning of the irradiation beam between the two angular orientations of the irradiation beam results in a delivered power density lower than the power density threshold at all positions of the window subjected to the irradiation beam.

4. The method of claim 1, wherein:
    the irradiation beam has an areal current density;
    the vacuum window has an areal current density threshold beyond which the vacuum window fails when subjected to, at a fixed position on the vacuum window, the areal current density beyond a pre-determined irradiation duration;
    the scanning of the irradiation beam between the two angular orientations of the irradiation beam results in a delivered power density lower than the power density threshold at all positions of the window subjected to the irradiation beam.

5. The method of claim 1 further comprising:
    accelerating particles to obtain the irradiation beam; and
    directing the irradiation beam toward a vacuum window.

6. The method of claim 1 further comprising generating bremsstrahlung radiation using the irradiation beam, wherein the bremsstrahlung radiation strikes the target until the stop criterion is met.

7. The method of claim 1, wherein scanning the irradiation beam repetitively back and forth between the two angular orientations of the irradiation beam as the irradiation beam strikes a vacuum window and traverses the vacuum window includes scanning an electron beam.

8. The method of claim 1 further comprising determining when the stop criterion is met.

9. The method of claim 8, wherein the stop criterion is a pre-determined irradiation dose delivered to the target and determining when the stop criterion is met includes determining the irradiation dose delivered to the target.

10. The method of claim 8, wherein the stop criterion is a transmutation of an element of the target into a transmutated element and determining when the stop criterion is met includes determining when a desired yield of transmutated element is attained.

11. The method of claim 8, wherein the stop criterion is a chemical change of an element of the target and determining when the stop criterion is met includes determining an extent of the chemical change of the element of the target and comparing the extent of the chemical change to a desired extent of chemical change.

12. The method of claim 8, wherein the stop criterion is a physical change of an element of the target and determining when the stop criterion is met includes determining an extent of the physical change of the target and comparing the extent of the physical change to a desired extent of physical change.

13. The method of claim 12, wherein the physical change includes one or more than one of a densification of the target, a vaporization of the target and a melting of the target.

14. The method of claim 1, wherein the stop criterion is an irradiation duration.

15. The method of claim 1, wherein synchronizing, to each other, the scanning of the irradiation beam and the moving of the target to maintain alignment between the irradiation beam and the target during the scanning of the irradiation beam and the moving of the target includes synchronizing the scanning of the irradiation beam to the moving of the target.

16. The method of claim 14, wherein synchronizing the scanning of the irradiation beam to the moving of the target includes sensing the position of the target to obtain a sensed position, and controlling the scanning of the irradiation beam in accordance with the sensed position.

17. The method of claim 1, wherein synchronizing, to each other, the scanning of the irradiation beam and the moving of the target to maintain alignment between the irradiation beam and the target during the scanning of the irradiation beam and the moving of the target includes synchronizing the moving of the target to the scanning of the irradiation beam.

18. The method of claim 17, wherein synchronizing the moving of the target to the scanning of the irradiation beam includes sensing the position of the irradiation beam to obtain a sensed position and moving the target in accordance with the sensed position.

19. A method of irradiating a target, the method comprising:

provining a particle accelerator, the particle accelerator having a vacuum window;

controlling the particle accelerator to generate an irradiation beam and to scan the irradiation beam repetitively back and forth between two angular orientations of the irradiation beam as the irradiation beam strikes the vacuum window and traverses the vacuum window;

mounting the target to a translation stage and controlling the translation stage to move the target, along a straight line, repetitively back and forth between two target positions;

aligning the target and the irradiation beam to each other;

synchronizing, to each other, the scanning of the irradiation beam and the moving of the target along the straight line to maintain alignment between the irradiation beam and the target during the scanning of the irradiation beam and the moving of the target;

shutting down the irradiation beam when a stop criterion is met.

* * * * *